United States Patent [19]
Bell et al.

[11] 4,438,271
[45] Mar. 20, 1984

[54] 2-ETHYLSULFONYL PYRIDINE 1-OXIDE DERIVATIVES

[75] Inventors: Allyn R. Bell; Arthur M. P. Doweyko, both of Cheshire; John A. Minatelli, Watertown, all of Conn.

[73] Assignee: Uniroyal, Inc., New York, N.Y.

[21] Appl. No.: 318,550

[22] Filed: Nov. 5, 1981

[51] Int. Cl.$^3$ ................ C07D 211/72; C07D 211/84; C07D 213/62
[52] U.S. Cl. ........................................ 546/294; 71/94
[58] Field of Search ........................................ 546/294

[56] References Cited
FOREIGN PATENT DOCUMENTS
28921  5/1981  European Pat. Off. ............ 546/294

Primary Examiner—Henry R. Jiles
Assistant Examiner—Robert C. Whittenbaugh
Attorney, Agent, or Firm—Marvin Bressler

[57] ABSTRACT

Superior herbicidal compounds are provided having the formula:

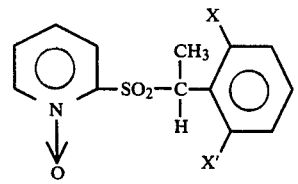

wherein X and X' are the same or different and are selected from the group consisting of chloro and fluoro.

3 Claims, No Drawings

2-ETHYLSULFONYL PYRIDINE 1-OXIDE DERIVATIVES

This invention relates to certain dihalophenyl substituted ethylsulfonyl pyridine 1-oxides and a method for using the same. Said compounds possess superior herbicidal activity against certain weeds, including nutsedge and reduced phytotoxic effect on soy beans.

The following references are of interest:

W. Walter et al., Liebig's Ann., 695, 77 (1966), disclose 2-(phenylmethylsulfinyl)pyridine N-oxide (also called 2-benzylsulfinylpyridine N-oxide) and 2-(phenylmethylsulfonyl)pyridine N-oxide (also called 2-benzylsulfonylpyridine N-oxide), but no utility for these chemicals is disclosed.

U.S. Pat. No. 3,107,994, Rawlings et al., Oct. 22, 1963, discloses certain herbicidal 2-(alkenylthio)pyridine N-oxides, while U.S. Pat. No. 3,155,671 D'Amico, Nov. 3, 1964, discloses certain heribicidal benzyl 2-thiopyridine N-oxides.

The state of the art is further illustrated by such references as E. Shaw et al., JACS 72, 4362 (1950) and U.S. Pat. No. 3,772,307, Kaminsky et al., Nov. 13, 1973.

U.S. Pat. Nos. 3,960,542 and 4,019,893 disclose generically the compounds of this invention but do not mention these chemicals specifically nor do these two references foreshadow or anticipate the exceptional herbicidal activity of the instant chemicals.

In accordance with the invention there are provided new herbicidally effective compounds of the formula

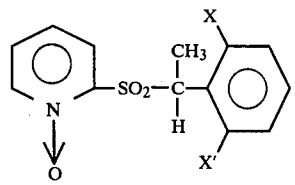

wherein X and X' are the same or different and are chloro and fluoro.

Weeds compete with crops of light, moisture, nutrients and space. Thus, weeds inhibit the production of foliage, fruit or seed of agricultural crops. The presence of weeds may also reduce the quality of the harvested crop and reduce harvesting efficiency. Weed control is essential for maximum production of many agronomic and horticultural crops including soybeans (*Glycine max* L.) peanuts (*Arachis hypogaea* L.) flax (*Linum usitatissium* L.) and cotton (Gossypium sp.).

Surprisingly the above compounds posses unexpected superior herbicidal activity against nutsedge (*Eyperus rotundus* L.) and reduced phytotoxic effect on soybeans while providing at least essentially equivalent control of other known compounds such as those disclosed in U.S. Pat. No. 3,960,542, of other common weeds. Such as switch grass, wild oats, green foxtail, barnyard grass, yellow foxtail, and crab grass.

The procedures for using the present 2-sulfonyl pyridine N-oxide derivatives as herbicides may be in accordance with conventional agriculture practice. The chemicals are ordinarily applied as formulations containing a carrier and/or surface-active agent. The formulation may contain more than one of the described pyridine 1-oxide derivatives if desired; other active herbicides may be included in the formulation as well.

Thus, the chemical may be impregnated on finely divided or granular inorganic or organic carriers such as attapulgite clay, sand, vermiculite, corn cobs, activated carbon or other granular carriers known in the art. The impregnated granules may then be spread on the soil. Furthermore, the chemical may be formulated as a wettable powder by grinding it into a fine powder and mixing it with an inactive powdered carrier to which a surface active dispersing agent has been added. Typical powdered solid carriers are the various mineral silicates, e.g., mica, talc, pyrophyllite and clays. The wettable powder may then be dispersed in water and sprayed on the soil surface or weeds. Similarly, an emulsifiable concentrate may be prepared by dissolving the chemical in a solvent such as benzene, toluene, or other aliphatic or aromatic hydrocarbon to which a surface active dispersant agent has been added. The emulsifiable concentrate may then be dispersed in water and applied by spraying. Suitable surface activity agents are well known to those skilled in the art and reference may be had to McCutcheon's Detergents and Emulsifiers, 1970, Allured Publishing Corp., Ridgewood, N.J.; or Hoffman et al. U.S. Pat. Nos. 2,614,916, cols. 2 to 4 and 2,547,724, cols. 3 to 4, for example of appropriate surface active agents. The concentration of active chemical in the formulation may vary widely, e.g., from 1 to 95%. The concentration of active chemical in dispersions applied to the soil or foliage is almost invariably from 0.002% to 75%. The chemical is frequently applied at rates of 0.10 to 25 pounds per acre. For use as a preemergence herbicide, the chemical is applied to soil which contains weed and crop seed (either to the surface of the soil or incorporated into the upper one to three inches of soil).

The most suitable rate of application in any given case will depend on such factors as soil type, soil pH, soil organic matter content, the quantity and intensity of rainfall before and after treatment, the air and soil temperature, light intensity and light duration per day. All of these factors can have an influence on the efficacy of the chemicals for use as herbicides.

The 2-sulfonylpyridine 1-oxide derivatives of the invention may be prepared from known compounds (see A. R. Katritsky, J. Chem. Soc., 191 [1957], U.S. Pat. Nos. 3,107,994 and 3,155,671 referred to above, and the E. Shaw et al. and W. Water et al. articles referred to above). The parent 2-thiopyridine 1-oxides are prepared by either of two procedures: (1) the reaction of 2-chloropyridine 1-oxide with the appropriate mercaptan in the presence of an acid acceptor such as an alkaline earth hydroxide; (2) reaction of the sodium salt of 2-mercaptopyridine 1-oxide with a suitable halide preferentially of, but not limited to, the benzyl type. The yields of the two procedures are comparable.

An alternate and useful synthetic route involves the oxidation of a 2-thiopyridine prepared by methods described in the literature. The oxidation involves the conversion of both the sulfur and nitrogen to their higher oxidation states in a single preparative step. In this case the products are sulfones as the sequence of oxidation proceeds from sulfide to sulfoxide to sulfone and to sulfone 1-oxide. The oxidant most generally employed, but not limited to, is 30–50% hydrogen peroxide in glacial acetic acid. In excess of three equivalents of peroxide is necessary.

The conversion of the 2-thiopyridine 1-oxide to the analogous sulfonyl compound is accomplished by employing one or two equivalents of an oxidizing agent selected from, but not necessarily limited to, hydrogen peroxide, peracetic acid, and the aromatic peroxy acids. The ratio of peroxide to substrate varies with the desired product.

The solvents employed vary with the oxidant as described in the literature (Katritsky and Lagowski, Chemistry of the Heterocyclic N-Oxides, Academic Press, 1971). Glacial acetic acid and water are preferred when hydrogen peroxide is used and a nonpolar solvent such as chloroform with the aromatic peroxy acids. When water is employed as a solvent a catalyst of the nature of a tungsten, vanadium, zirconium or molybdenum salt (U.S. Pat. Nos. 3,005,852, Freyermuth et al., Oct. 24, 1961, 3,006,962, Schutz et al., Oct. 31, 1961, 3,006,963, Buc et al. Oct. 31, 1961 and British Pat. No. 1,335,626, Eastman Kodak Co., Oct. 31, 1973) is generally used. Temperature and time are a function of the sulfide employed with the range varying from 50° to reflux in the case of water and acetic acid to 0° to 60° with chloroform.

Compounds of the invention may be used for selective control of various grasses and weeds including switch grass, wild oats, green foxtail, barnyard grass, yellow foxtail, crab grass and nutsedge. Most notably the compounds have a superior herbicidal effect on nutsedge, a weed that is difficult to control.

Application may be in aqueous solutions or suspensions which may be sprayed onto the soil surface prior to weed and crop emergence and before or after the crop seed is sown. The soil may receive a shallow tilling (less than 3 inches) after application of the chemical, but this is not required as it is with some preemergence herbicides. The compounds of this invention may also be applied by broadcast of a granular formulation prior to weed and crop emergence.

Compounds of this invention may be added as a "tank mix" to other herbicide solutions so that the number of different weed species controlled in a single application will be increased. The formulations of invention compounds may also include other herbicides so that the spectrum of weeds controlled by spray or granular application may be increased.

The following examples will serve to illustrate the practice of the invention in more detail.

EXAMPLE I

Preparation of 2-[1-(2,6-Dichlorophenyl)ethylsulfonyl]pyridine-1-oxide 2-(2,6-Dichlorophenyl)methylsulfonyl pyridine 1-oxide* (1.75 g, 5.5 mmol) was added in one portion to a stirring solution of 20 mls of dimethylformamide containing 0.24 g of sodium hydroxide and 0.77 g of dimethylsulfate (6.1 mmol). The mixture was allowed to stir at room temperature for 1 h, then poured into 300 ml of rapidly stirring water whereupon a precipitate formed. The precipitate was filtered off, washed with water, and air dried to afford 1.38 g product, m.p. 179°–183° (74% yield).

*This compound was prepared by the methods disclosed in U.S. Pat. No. 3,960,542 and U.S. Pat. No. 4,019,893, herewith enclosed by reference.

Analysis: IR, NMR Elemental: Calc: C 46.99; H 3.31; N 4.22. Found: C 46.35; H 3.46; N 4.31.

EXAMPLE II

Preparation of 2-[1-(2,6-Difluorophenyl)ethylsulfonyl]pyridine-1-oxide (A) Preparation of 2,6-Difluoroacetophenone 2,6-Difluorobenzonitrile (20.0 g, 0.14 mol) is dissolved in anhydrous diethyl ether (30 ml) and methyl magnesium bromide (154 ml of a 2.8 M solution, 0.43 mol) is added. The whole is warmed to reflux (35° C.) overnight (16 hrs.). Then the reaction mixture is quenched in ice-water (150 ml). The resultant mixture is heated to 75° C. for 3 hours and cooled. Pure product is then extracted from the mixture using methylene chloride (17.2 g, 76.7%).

(B) Preparation of 2,6-Difluoro-alpha-methylbenzyl alcohol 2,6-Difluoroacetophenone of (A) (17.2 g, 0.11 mol) is dissolved in isopropyl alcohol (50 ml) and NaBH$_4$ (2.0 g, 0.055 mol) is added. The resultant mixture is warmed to 60° C. for about 14 hours. A solution of NaOH (4.9 g, 0.12 mol) in water (20 ml) is then added. After 1 hour at 60° C., this reaction mixture is cooled and acidified with dilute HCl. Extraction with methylene chloride provided pure title product (14.9 g, 85.5%).

(C) Preparation of 2,6-Difluoro-alpha-methylbenzyl chloride 2,6-Difluoro-alpha-methylbenzyl alcohol of (B) (14.9 g, 0.094 mol) is dissolved in chloroform (50 ml) and warmed to 60° C. Thionyl chloride (22.4 g, 0.19 mol) is now added dropwise. The whole is kept at 60° C. for 4 hours then stirred overnight at room temperature. Excess thionyl chloride and chloroform are then removed on a rotary evaporator, resulting in pure title product (16.6 g, 99.8%).

(D) Preparation of 2-[1-(2,6-Difluorophenyl)ethylthio]pyridine 1-oxide 2,6-Difluoro-alpha-methylbenzyl chloride (16.6 g, 0.094 mol) is dissolved in ethanol (40 ml) and warmed to 75° C. A 40 percent solution of sodium omadine (38.5 g, 0.103 mol) is added dropwise over a period of 30 minutes maintaining a reaction temperature of 75° C. throughout. Once the addition is complete, the reaction mixture is kept between 75° C. and 80° C. for 2 hours. Thereafter the mixture is quenched in ice-water and crude product is filtered off. After recrystallization with ethyl acetate pure title product (10.65 g, 42.4%) is obtained; Melting Point 158°–160° C.

(E) Preparation of 2-[1-(2,6-Difluorophenyl)ethylsulfonyl]pyridine 1-oxide

2-[1-(2,6-Difluorophenyl)ethylthio]pyridine 1-oxide of (D) (6.65 g, 0.025 mol) is dissolved in methylene chloride (75 ml). Meta-chloroperoxybenzoic acid (85 percent) (11.1 g, 0.065 mol) is added. The mixture is refluxed for 16 hours. Then dilute base is added until the reaction mixture is basic, and the layers are separated. The organic layer is extracted once with 3 N NaOH (40 ml). The layers are separated and dried over MgSO$_4$. Methylene chloride is now removed leaving slightly impure product. Recrystallization with ethyl acetate gave pure title product (4.95 g, 66.6%); Melting Point 171°–173° C.

Chemical analysis: Calculated: C 52.17; H 3.70; N 4.68. Found: C 52.29; H 3.93; N 4.70.

EXAMPLE III

Preparation of
2-[1-(2-chloro-6-fluorophenyl)ethylsulfonyl]pyridine
1-oxide (A) Preparation of 2-chloro-6-fluoroacetophenone 2-chloro-6-fluorobenzonitrile (42.3 g, 0.27 mol) is dissolved in anhydrous diethyl ether (170 ml) and methyl magnesium bromide (291 ml of a 2.8 M solution, 0.82 mol) is added. The whole is warmed to reflux (35° C.) overnight (16 hrs.). Then the reaction mixture is quenched in ice-water (380 ml) followed by the addition of concentrated $H_2SO_4$ (95 ml). The resultant mixture is heated to 100° C. for 3 hours and stirred overnight at room temperature. Pure product is then extracted from the mixture using chloroform (45.0 g, 95.9%).

(B) Preparation of 2-chloro-6-fluoro-alpha-methyl-benzyl alcohol 2-chloro-6-fluoroacetophenone of (A) (45.0 g, 0.26 mol) is dissolved in isopropyl alcohol (98 ml) and $NaBH_4$ (4.9 g, 0.13 mol) is added. The resultant mixture is warmed to 55° C. for about 16 hours. A solution of NaOH 10.4 g, 0.26 mol) in water (41. ml) is then added. After 1 hour at 55° C., this reaction mixture is cooled and acidified with diluted HCl. Extraction with chloroform provided pure title product (45.1 g, 99.1%).

(C) Preparation of 2-chloro-6-fluoro-alpha-methyl-benzyl chloride 2-chloro-6-fluoro-alpha-methylbenzyl alcohol of (B) (45.1 g, 0.26 mol) is dissolved in chloroform (70 ml), and thionyl chloride (61.5 g, 0.52 mol) is added over a period of 30 minutes. The resultant mixture is refluxed for 16 hours. Excess thionyl chloroform are then removed on a rotary evaporator, resulting in pure title product (46.2 g, 92.6%).

(D) Preparation of 2-[1-(2-chloro-6-fluorophenyl)ethylthio]pyridine 1-oxide 2-chloro-6-fluoro-alpha-methylbenzyl chloride (46.2, 0.24 mol is dissolved in ethanol (120 Ml) and warmed to 75° C. A 40 percent solution of sodium omadine (98.1 g, 0.26 mol) is added dropwise over a period of 30 minutes maintaining a reaction temperature of 75° C. throughout. Once the addition is complete, the reaction mixture is kept at 75° C. for 2 hours and then stirred at room temperature for 16 hours. Thereafter the mixture is quenched in ice-water and crude product is filtered off. After recrystallization with ethyl acetate pure title product (27.7 g, 40.8%) is obtained; Melting Point 142°–144° C.

Chemical Analysis Calculated: C: 55.03; H: 3.91; N: 4.93. Found: C: 55.11; H: 4.10; N: 4.92.

(E) Preparation of 2-[1-(2-chloro-6-fluorophenyl)ethylsulfonyl]pyridine 1-oxide

2-[1-(2-chloro-6-fluorophenyl)ethylthio]pyridine 1-oxide of (D) (27.7 g, 0.1 mol) is dissolved in methylene chloride (190 ml). Meta-chloroperoxybenzoic acid (85 percent) (43.7 g, 0125 mol) is added over a period of 15 minutes. The mixture is refluxed for 16 hours. Then dilute base is added until the reaction mixture is basic and the layers are separated. The organic layer is extracted once with 3 N NaOH (100 ml). The layers are separated and dried over $MgSO_4$. Methylene chloride is now removed leaving slightly impure product. 200 ml of ethyl acetate is added, and product is filtered off. 19.8 g (64.2%) of pure title material is obtained. M.P. 189°–191° C.

Chemical Analysis Calculated: C: 49.45; H: 3.51; N: 4.43. Found: C: 49.26; H: 3.51; N: 4.39.

The herbicidal activity of the instant compound was evaluated in comparison with known similar substituted pyridine 1-oxides as described in Example IV below.

In U.S. Pat. Nos. 3,960,542 and 4,019,893 a total of 114 compounds are disclosed and tested as herbicides for the control of rough pigweed (*Amaranthus retroflexus* L.), purslane (*portulaca oleracea* L.) or jimsonweed (*Datura stramonium* L.), tall morningglory (*Ipomea purpurea* (L.) Roth), crabgrass (*Digitaria ischaemum*) (Schweb. Muhl.), barnyard grass (*Echinochloa crusgalli* (L.) Beauv.) and giant foxtail (*Setaria faberi* Herrm.) at a 10 lbs/acre (11.2 kg/ha) rate. In U.S. Pat. No. 4,019,893 Table III (see also U.S. Pat. No. 3,960,542 Table III) the testing results are summarized indicating that certain compounds have an overall activity of 575 or higher out of a maximum of 600. These exceptional chemicals are listed in Table I below.

TABLE I

General Formula

| No. | '893 No. | '542 No. | Chemical Name of W-Radical | Total Activity |
|---|---|---|---|---|
| 1 | 102 | 55 | 1-(1-naphthyl)ethylsulfonyl | 600 |
| 2 | 1 | 1 | 2,5-dimethylphenylmethylsulfonyl | 600 |
| 3 | 9 | 9 | 1-phenylethylsulfonyl | 590 |
| 4 | 16 | 16 | 1-(4-fluorophenyl)ethylsulfonyl | 583 |
| 5 | 13 | 13 | 2,3,6-trichlorophenylmethylsulfinyl | 575 |

EXAMPLE IV

To illustrate effectiveness of the described sulfonyl pyridine-1-oxide as preemergence herbicides, 25 mg chemical is dissolved in 10 ml organic solvent (e.g. acetone) to which 15 mg conventional emulsifying agent (e.g., ethoxylated sorbitan monolaminate "Tween 20") is added. The solution is diluted to 100 ml with distilled water. Five milliliters of this 250 ppm (parts per million) solution is diluted to 100 ml (12.5 ppm) with distilled water. The chemical is applied at the rate of ½ lb/a (pounds per acre) by drenching 46 ml of the 12.5 ppm solution on the surface of soil in 4½ inch diameter plastic pots which had been sown with the following weed seeds: Switchgrass (*Panicum virgatum* L.), Wild Oats (*Avena fatua* L.), Green Foxtail (*Setaria viridis* (L.) Beauv.), Barnyardgrass (*Echinochloa crus-galli* (L.) Beauv.), Yellow Foxtail (*Setaria lutescens* (Weigel) Hubb.), Crabgrass (*Digitaria ischaemum* (Schreb) Muhl.), and nutsedge (Cyperus s.p.p.) The percent control of the weed is determined two weeks after treatment. Table II shows the herbicidal results of compounds of this invention compared with the best known compounds, expressed as percent weed control.

TABLE II

| Example No.[1] | SG | WO | GF | BG | YF | CG | NS[2] | Total Activity | Improvement %[3] |
|---|---|---|---|---|---|---|---|---|---|
| 1 | 85 | 100 | 100 | 100 | 100 | 100 | 0 | 585 | — |

TABLE II-continued

| Example No.[1] | SG | WO | GF | BG | YF | CG | NS[2] | Total Activity | Improvement %[3] |
|---|---|---|---|---|---|---|---|---|---|
| 2 | 90 | 100 | 100 | 100 | 95 | 100 | 0 | 585 | — |
| 3 | 100 | 25 | 95 | 90 | 95 | 100 | 50 | 555 | — |
| 4 | 85 | 65 | 95 | 100 | 85 | 100 | 0 | 530 | — |
| 5 | 100 | 85 | 100 | 100 | 100 | 100 | 0 | 585 | — |
| I | 100 | 95 | 90 | 100 | 100** | 100 | 80 | 665 | 13.7 |
| II | 100* | 100* | 100* | 100* | 100*** | 100* | 50 | 650 | 11.1 |
| III | 100 | 100 | 100 | 100 | 100** | 100 | 100 | 700 | 19.6 |

Remarks:
[1] Examples 1, 2, 3, 4 and 5 are known compounds of Table 1. Examples I, II and III are this invention.
[2] SG = Switchgrass; WO = wild oats; GF = green foxtail; BG = barnyard grass; YF = yellow foxtail; CG = crabgrass, and NS = nutsedge.
[3] Improvement in total activity over best known chemical (percent). *Tested at 0.25 lbs/a (0.28 kg/ha). **Tested on goosegrass.

The data demonstrate that the chemicals of this invention unexpectedly have improved overall activity in comparison with the best known compounds and/or excel in the control of nutsedge.

We claim:

1. 2-[1-(2,6-Dichlorophenyl)ethylsulfonyl]pyridine 1-oxide.
2. 2-[1-(2,6-Difluorophenyl)ethylsulfonyl]pyridine 1-oxide.
3. 2-[1-(2-Chloro-6-fluorophenyl)ethylsulfonyl]pyridine 1-oxide.

* * * * *